(12) United States Patent
Bruder et al.

(10) Patent No.: US 6,379,953 B1
(45) Date of Patent: Apr. 30, 2002

(54) LIGANDS THAT MODULATE DIFFERENTIATION OF MESENCHYMAL STEM CELLS

(75) Inventors: Scott P. Bruder, Owings Mills; Neelam Jaiswal, Ellicott City, both of MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/452,142

(22) Filed: Dec. 1, 1999

Related U.S. Application Data

(62) Division of application No. 09/141,882, filed on Aug. 28, 1998, now Pat. No. 6,022,540.
(60) Provisional application No. 60/057,928, filed on Sep. 4, 1997.

(51) Int. Cl.[7] ............................. C12N 5/02; C07K 16/00; A01N 63/00; A61K 39/395

(52) U.S. Cl. ................... 435/325; 424/93.7; 424/156.1; 424/152.1; 424/135.1; 424/198.1; 435/372; 435/384; 435/397; 530/350; 530/388.2; 530/389.1

(58) Field of Search ............................. 435/325, 375, 435/376, 384, 397, 372; 530/356, 388.2, 389.1; 424/156.1, 152.1, 135.1, 198.1, 93.7

*Primary Examiner*—David Saunders
*Assistant Examiner*—Amy DeCloux
(74) *Attorney, Agent, or Firm*—Elliot M. Olstein; Raymond J. Lillie

(57) ABSTRACT

Disclosed are compositions and methods for accelerating the differentiation of human MSCs into the osteogenic lineage with resultant enhanced de novo bone formation. This makes possible improved methods for bone defect repair. Thus, one aspect of the invention is a method for accelerating the differentiation of ALCAM-bearing hMSCs into the osteogenic lineage by contacting such hMSCs with a ligand that binds to activated leukocyte-cell adhesion molecule (ALCAM) on a single hMSC. Preferably, the ligand is a $F_{ab}$ fragment of a monoclonal antibody expressed by the hybridoma of ATCC Accession No. NB 11789.

9 Claims, 5 Drawing Sheets

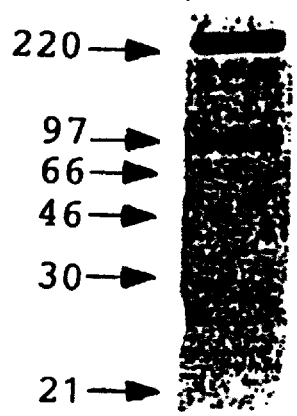
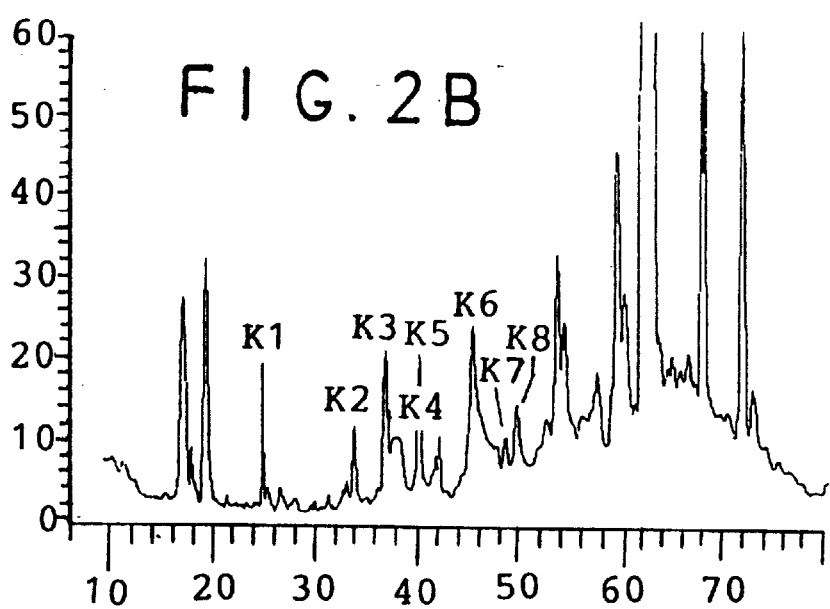
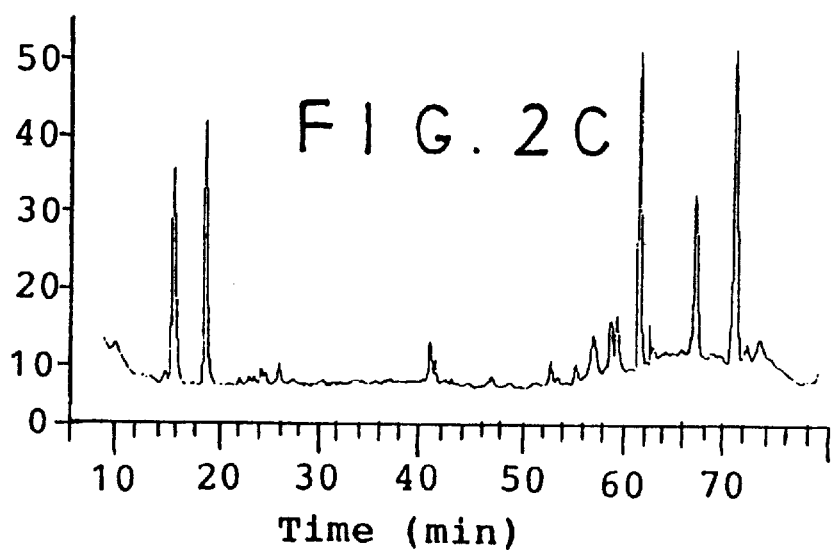

LIGANDS THAT MODULATE DIFFERENTIATION OF MESENCHYMAL STEM CELLS

This is a Divisional of application Ser. No. 09/141,882 filed Aug. 28, 1998, now U.S. Pat. No. 6,022,540 which claims priority based on provisional application Ser. No. 60/057,928, filed Sep. 4, 1997.

This application is based on prior U.S. application Ser. No. 60/057,928 filed on Sep. 4, 1997.

BACKGROUND OF THE INVENTION

Mesenchymal stem cells (MSCs) have the capacity to develop into a variety of tissue types including bone, cartilage, tendon, muscle, fat and hematopoietic-supportive stroma. Techniques for the isolation of human and animal MSCs have been described as have techniques for directing their differentiation into, inter alia, the osteogenic lineage. These cells have also been shown to retain their developmental potential following extensive subcultivation in vitro (Bruder et al., 1997b), supporting their characterization as stem cells.

Although several monoclonal antibodies (McAb) that react with the surface of human mesenchymal stem cells (hMSCs) in culture have been described (Haynesworth et al., 1992a), the molecular identity of their respective antigens was not addressed. Recently, a new series of McAbs directed against the surface of human MSCs undergoing osteoblastic differentiation was reported (Bruder et al., 1997a). One of these McAbs, referred to as SB-10, reacts with the surface of human MSCs during fetal long bone and calvarial development, as well as the surface of marrow-derived MSCs in culture prior to differentiation. Immunoreactivity is lost during lineage progression when the osteoblast marker alkaline phosphatase (APase) is expressed. The SB-10 antigen has been observed not only in the outer periosteum of developing bones, but also in the developing brain, lung, and esophagus (Bruder et al., 1997a).

SUMMARY OF THE INVENTION

In one aspect the invention provides a method for accelerating the rate of differentiation of human mesenchymal stem cells, which method comprises contacting such human mesenchymal stem cells with an agent that inhibits cell-to-cell interaction of such human mesenchymal stem cells. Preferably the agent disrupts cell-to-cell binding. Preferred embodiments include monovalent ligands for human mesenchymal stem cell surface molecules and polynucleotides complementary to nucleic acid sequences coding for such cell surface molecules.

In another aspect the invention provides a method for inhibiting the rate of differentiation of human mesenchymal stem cells, which method comprises contacting such human mesenchymal stem cells with an agent that stimulates cell-to-cell interaction of such human mesenchymal stem cells. Preferably the agent enhances cell-to-cell binding. Preferred embodiments include polyvalent ligands for human mesenchymal stem cell surface molecules.

Also contemplated is the genetic manipulation of human mesenchymal stem cells to augment their production of agents that modulate cell-to-cell interaction, such as homophilic surface molecules, e.g. ALCAM.

In arriving at the present invention, the inventors have isolated, by immunopurification, the SB-10 antigen, and identified it as activated leukocyte-cell adhesion molecule (ALCAM). Thus, in a particularly preferred embodiment, the invention provides a method for accelerating the osteogenesis of an ALCAM-bearing mesenchymal stem cell which comprises contacting said mesenchymal stem cell with a ligand that binds with ALCAM on a single mesenchymal stem cell. The use of whole antibody is not contemplated, as cell-cell-binding does not provide the acceleration of osteogenesis observed in accordance with the invention. Preferred embodiments include those where the ligand is an $F_{ab}$ fragment of an antibody to ALCAM (e.g. an $F_{ab}$ fragment of the monoclonal antibody produced by the hybridoma cell line of ATCC Accession No. HB 11789), a single chain antibody to ALCAM and an ALCAM or fragment thereof. Preferably, the MSCs are human and, most preferably, autologous to the intended recipient. Any of the agents that are known to induce commitment and differentiation into the osteogenic lineage are suitable for use with respect to the present invention.

The cell line culture identified as SB-10 has been deposited (in accordance with the requirements of the Budapest Treaty for patent purposes) with the American Type Culture Collection, 12301 Parklawn Drive, Rockville, Md. 20852 (deposit date Jan. 10, 1995), and is assigned the ATCC Accession number HB-11789.

In another aspect, the invention provides a method for accelerating the in vivo formation of bone from mesenchymal stem cells that have been exposed to an osteoinductive agent by contacting said mesenchymal stem cells with a ligand that binds with ALCAM on a single mesenchymal stem cell. The preferred embodiments are the same as those described for the above aspect.

In another aspect, the invention provides a composition comprising an ALCAM-bearing mesenchymal stem cell and a ligand that binds with ALCAM on a single mesenchymal stem cell. The preferred embodiments are the same as those for the above aspects.

In another aspect, the invention provides a method for accelerating the in vivo formation of bone in an individual in need thereof which comprises administering to said individual, at the site where such bone is to be formed, a composition comprising ALCAM-bearing mesenchymal stem cells and ligand that binds with ALCAM on a single mesenchymal stem cell. The preferred embodiments are the same as those for the above aspects.

In another aspect, the invention provides a composition comprising an ALCAM bearing mesenchymal stem cell, an agent that is osteoinductive for said mesenchymal stem cell and a ligand that binds with ALCAM on a single mesenchymal stem cell. This will produce bone either in vivo or in vitro. The preferred embodiments are the same as those for the above aspects.

In another aspect, the invention provides a method for accelerating the in vivo formation of bone in an individual in need thereof which comprises administering to said individual, at the site where such bone is to be formed, a composition comprising ALCAM-bearing mesenchymal stem cells, an agent that is osteoinductive for said mesenchymal stem cells and ligands that bind with ALCAM on a single mesenchymal stem cell. The preferred embodiments are the same as those for the above embodiments.

BRIEF DESCRIPTION OF THE DRAWINGS

FIG. 1. Immunoblotting of the SB-10 antigen on cultured human MSCs. Plasma membrane protein extracts were prepared as described herein, separated by electrophoresis on a continuous 10% SDS-polyacrylamide gel, transferred to a PVDF membrane, and probed with SB-10 (lanes 1–3)

or control antibody SB-1 (lanes 4–6). Five μg of protein extract was added to each lane. Samples were loaded under native conditions (lanes 1 and 4), following boiling (lanes 2 and 5), and after boiling and reduction (lanes 3 and 6). The electrophoretic mobility of reduced molecular mass standards in kDa is shown to the left in this and all subsequent immunoblots.

FIG. 2. Immunopurification of the SB-10 antigen, and HPLC separation of digested peptides.

FIG. 2A. CHAPS-soluble membrane proteins from human MSCs were incubated with purified SB-10, and the complexes immunoprecipitated by the addition of protein-G agarose. After washing, the affinity-bound material was eluted by boiling in SDS-sample buffer. Following unreduced SDS-PAGE, the gel was stained with Coomassie-G.

FIG. 2B. The ~99 kDa bands were excised, and the protein digested by enzymatic treatment as described below. The recovered peptides were separated by reverse-phase HPLC. Collected peaks were referred to as K1 to K8, and were subjected to amino-terminal protein sequence analysis. The results are shown in Table I.

FIG. 2C. HPLC profile of a control portion of polyacrylamide excised from the same gel.

Figure 3:
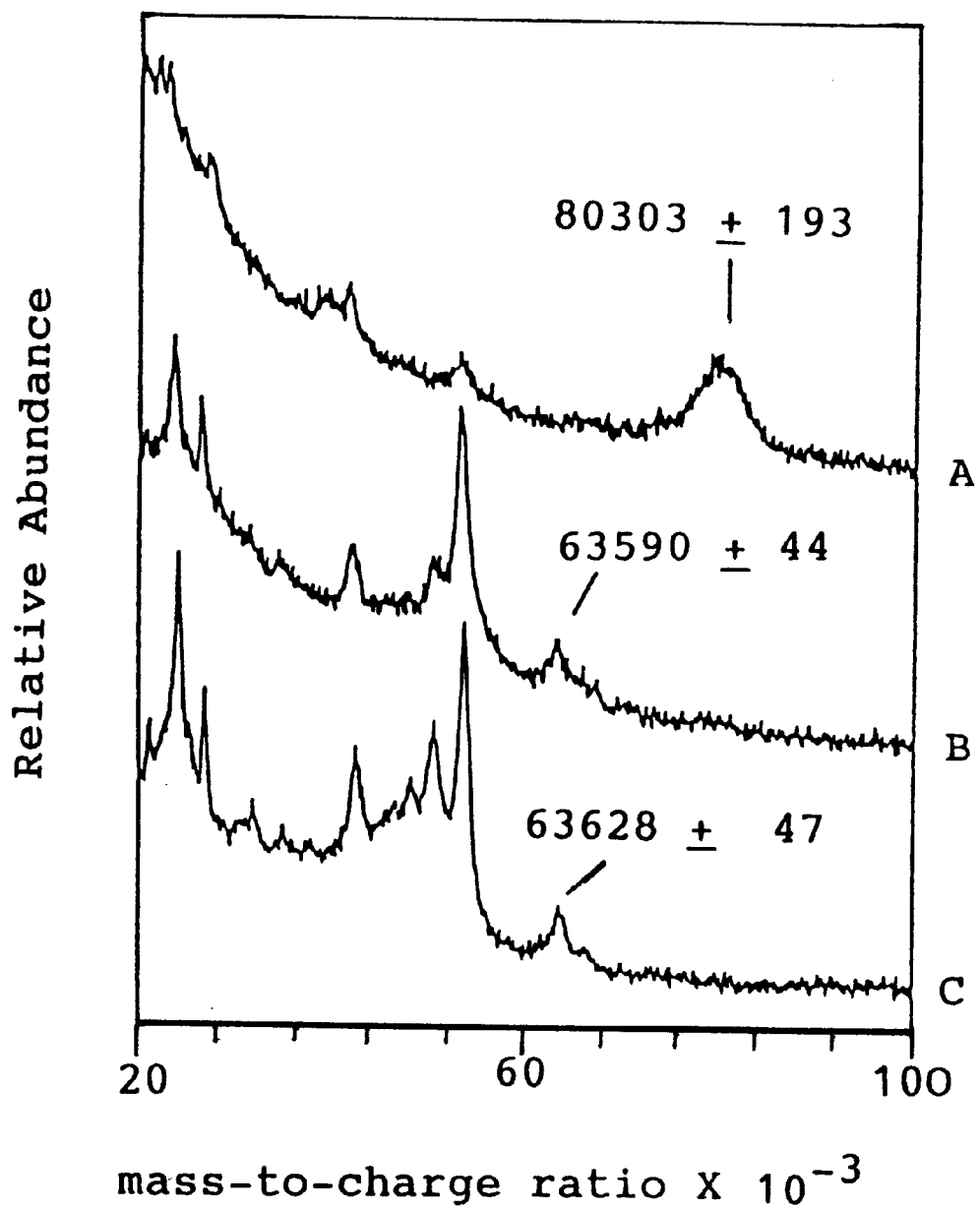

FIG. 3. Deglycosylation of the SB-10 antigen, ALCAM, monitored by MALDI-TOF mass spectrometry. (A) SB-10 antigen, 500 shots accumulated. The average mass and standard deviation for reduced SB-10 antigen from 5 measurements is shown to be 80,303 Da. The ion corresponding to a molecular weight of 42,300 is an artifact observed in MALDI-TOF mass spectra of protein G immunoprecipitates. (B) Reduced SB-10 antigen, alkylated with 4-vinylpyridine and digested with N-glycosidase F, 244 shots accumulated. Ions produced by polypeptides of molecular weight 24,000 and 53,500 Da correspond to reduced and 4-vinylpyridine alkylated SB-10 antibody light and heavy chains, respectively. The artifact observed in (A) is also present. The average mass and standard deviation for de-N-glycosylated SB-10 antigen from 4 measurements is shown. (C) Reduced, alkylated, de-N-glycosylated SB-10 antigen treated with neuraminidase and O-glycanase, 153 shots accumulated. Peak assignments are the same as in (B) with the average mass and standard deviation for fully deglycosylated SB-10 from 4 measurements shown.

FIG. 4. Immunoblotting of human MSC extracts and immunoprecipitates with SB-10 and J4-81.

Figure 4A:
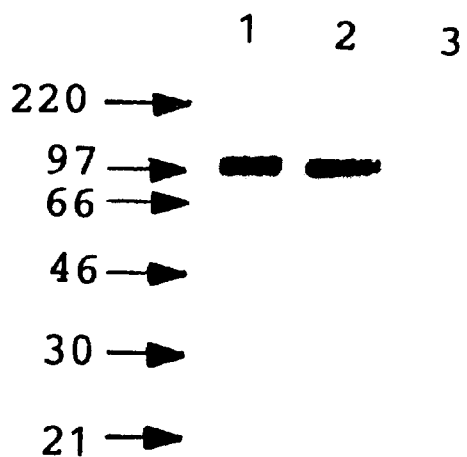

FIG. 4A. CHAPS-soluble membrane proteins from human MSCs were separated by SDS-PAGE under non-reducing conditions, transferred to a PVDF membrane, and probed with SB-10 (lane 1), J4-81 (lane 2), and irrelevant SB-1 control (lane 3).

Figure 4B:
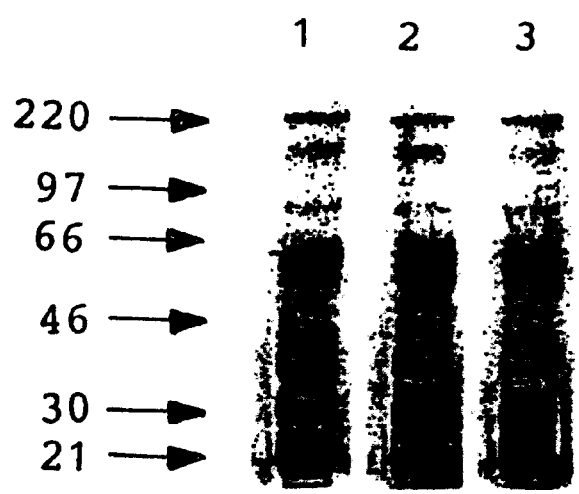

FIG. 4B. Immunoblot of the SB-10 immunoprecipitation from a CHAPS-soluble membrane extract of human MSCs. Following elution and SDS-PAGE under non-reducing conditions, the material was transferred to a PVDF membrane. Individual lanes were probed with SB-10 (lane 1), J4-81 (lane 2), or SB-1 (lane 3).

FIG. 5. PCR amplification of ALCAM fragments in various human and animal cells, and Northern blot analysis of ALCAM mRNA expression.

Figure 5A:
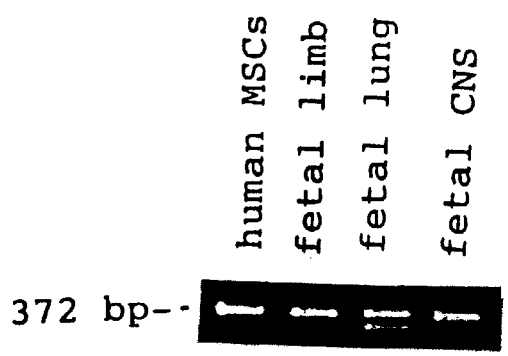

FIG. 5A. Total RNA was extracted from human MSCs, and human fetal limb periosteum, fetal lung, and fetal CNS. Samples were reverse transcribed into cDNA, and amplified by using an oligonucleotide primer pair coding for a 372 bp fragment specific for ALCAM. Reaction products were visualized on ethidium bromide-stained agarose gels.

Figure 5B:
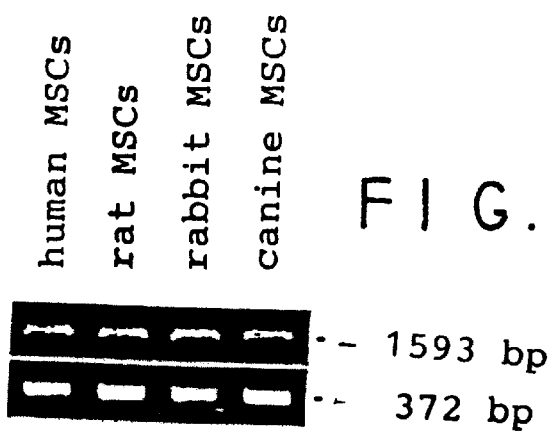

FIG. 5B. Total RNA was extracted from human, rat, rabbit, and canine MSC cultures, and subjected to RT-PCR as described above. PCR amplification of the 372 bp fragment was performed, along with amplification of a specific 1593 bp fragment.

Figure 5C:
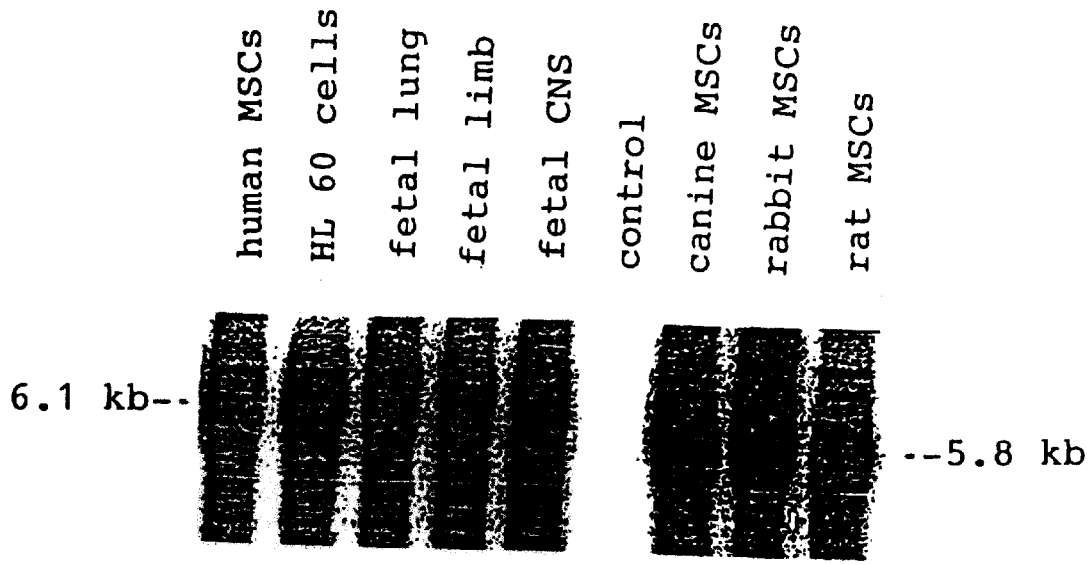

FIG. 5C. Northern blot analysis. Twenty μg of total RNA from human MSCs, HL60 cells, fetal lung, fetal limb, fetal CNS, control bacteria, and MSCs from canine, rabbit, and rat was loaded in each lane. The 372 bp ALCAM fragment was double labeled and used to probe the membrane. The size of the reactive mRNA was determined using an RNA ladder and probing it with a fragment of lambda DNA (data not shown).

DETAILED DESCRIPTION OF THE PREFERRED EMBODIMENTS

A developmentally regulated cell surface antigen has been identified on human mesenchymal stem cells that is conserved across multiple species. The monoclonal antibody SB-10, which recognizes a surface antigen on human MSCs in vivo and in vitro (Bruder et al., 1997a), has now been shown to specifically react with the type I membrane glycoprotein known as activated leukocyte-cell adhesion molecule (ALCAM). First discovered on thymic epithelial cells (Patel et al., 1995), activated T cells, B cells, and monocytes (Bowen et al., 1995), ALCAM is a member of the immunoglobulin superfamily of CAMs, and has been established as a ligand for CD6 (Bowen et al., 1995), a member of the scavenger receptor cysteine-rich family of proteins (Resnick et al., 1994). ALCAM has significant peptide sequence homology with BEN (SC-1/DM-GRASP), a neuronal protein in chick (Tanaka et al., 1991; Burns et al., 1991; Pourquie et al., 1992), neurolin, its fish homologue (Laesing et al., 1994), and MUC18, a cell surface marker of human melanoma tumor progression (Lehman et al., 1989).

Mesenchymal stem cells can be obtained from bone marrow at sites such as the iliac crest, femora, tibiae, spine, rib or other medullary spaces. Other sources of human mesenchymal stem cells include embryonic yolk sac, placenta, umbilical cord, periosteum, fetal and adolescent skin, and blood. The use of both autologous and allogeneic MSCs is contemplated.

As used in the Examples set forth below, mesenchymal stem cells were isolated from fresh bone marrow aspirates of rat, rabbit, dog, and human sources as previously described (Dennis et al., 1992; Kadiyala et al., 1997; Lennon et al., 1996; Wakitani et al., 1994; Haynesworth et al., 1992b), and cultivated in Dulbecco's modified Eagle's medium containing 10% fetal bovine serum. Cells were grown in 185 cm$^2$ flasks, and serially passaged when they approached confluence. Human myelomonocytic HL60 cells were obtained from American Type Culture Collection, and maintained in Iscove's modified Dulbecco's medium plus 10% fetal bovine serum. Monoclonal antibodies used were SB-10 (Bruder et al., 1997a), SB-1 (Bruder and Caplan, 1990) and J4-81 (Pesando et al., 1986), which was a gift from J. Pesando. McAbs were purified by Protein-G agarose (Boehringer Mannheim) affinity chromatography. Antibody $F_{ab}$ fragments were prepared from purified McAbs by digestion with papain followed by affinity purification (Pierce).

The composition can also contain additional components, such as osteoinductive factors. The osteoinductive factors include any that are now known and any factors which are later recognized to have osteoinductive activity. Such osteoinductive factors include, for example, dexamethasone, ascorbic acid-2-phosphate, β-glycerophosphate and TGF superfamily proteins, such as the bone morphogenic proteins (BMPs). The composition can also contain antibiotic, antimycotic, antiinflammatory, immunosuppressive and other types of therapeutic, preservative and excipient agents.

Various cases require a spectrum of the amount, frequency and duration of ALCAM ligand administration depending, inter alia, the size of the defect to be repaired, the type of ligand to be administered and the duration between inception of the disorder and beginning of treatment.

It is preferred that only a single dose of ligand be administered whenever possible. This can be administered to MSCs in vitro at the inception of culture and osteogenesis or MSCs can be administered with the ligand to the site intended for in vivo generation of bone. When osteogenesis is induced in culture, to provide osteoblasts for in vivo implant, it is desirable that the MSCs be cultured for at least about 6–12 days in the presence of a uniform concentration of ligand during the culture period. The ligand concentration should be at least about 2 $\mu$g/ml of culture medium, more preferably at least about 5 $\mu$g/ml of medium and up to about 50 $\mu$g/ml of medium. A concentration of about 10 $\mu$g/ml is currently believed to be in the optimal range. When multiple ligand administrations are deemed necessary, such as when the medium is changed, on a continuous or intermittent basis, the minimal concentration and duration of ligand administration should be such as will produce a population of osteoblasts sufficient for the intended treatment. For example, at 10 $\mu$g/ml (assuming 2 ml of medium per culture well and an initial MSC count of 30,000 cells/well) this represents about 0.7 nanograms or 700 picograms of ligand per cell.

The MSCs are administered after culture expansion or induction of osteogenesis and preferably in combination with similar concentrations of ligand in a pharmaceutically acceptable medium and format by any of several routes of administration. In a preferred embodiment the cells are administered by an arthroscopic procedure. They can also be administered in a ceramic cube which is situated in a bone defect area where new bone is to be generated.

The invention provides a method for bone formation in an individual in need thereof by administering human mesenchymal stem cells and/or osteoblasts with a matrix which supports bone formation. The matrix is preferably selected from a ceramic or a resorbable biopolymer. The ceramic can be in particulate form or can be in the form of a structurally stable, three-dimensional implant. The structurally stable, three-dimensional implant can be, for example, a cube, cylinder, block or an appropriate anatomical form. The resorbable biopolymer can be, for example, a fibrin, hyaluronan, gelatin, collagen or cellulose matrix, can be in the form of a powder, strip, gel, web or sponge, and is preferably a bovine skin-derived gelatin. The matrix medium, vehicle excipient or carrier can be any of those known to be pharmaceutically acceptable for administration to a patient, particularly locally at the site at which new bone growth is to be induced. Such media can include also liquid media, for example, DMEM, sterile saline, dextrose in sterile water and any other physiologically acceptable isotonic liquid.

The following examples further illustrate, but are in no way a limitation of, the invention.

The experiments reported here include, inter alia, demonstration of a specific immunoreactivity of an identifiable antigen (SB-10 antigen) from hMSC plasma membrane with SB-10 antibody, purification and characterization of the SB-10 antigen, confirmation of the identity of SB-10 antigen with the activated leukocyte-cell adhesion molecule (ALCAM), molecular cloning of a full length ALCAM cDNA and acceleration of in vitro osteogenesis of human MSCs by SB-10 $F_{ab}$ antibody fragments. Thus, this provides the basis for enhancing the de novo production of bone in vivo.

EXAMPLE 1

Immunoblotting Analyses

MSCs cultured under known conditions (see Caplan and Haynesworth, U.S. Pat. No. 5,486,359) were scraped with a rubber policeman or flexible plastic spatula in a lysis buffer composed of 150 mM NaCl, 50 mM Tris, pH 7.4 with protease inhibitors of 10 mM EDTA, 1 mM PMSF, 1 $\mu$g/ml Aprotinin, and 1 $\mu$g/ml Leupeptin. Cells were sonicated for 30 sec on ice, the nuclei and debris were centrifuged to a pellet at 1,000×g for 10 min, and the supernatant was then centrifuged at 48,000×g for 2 hr at 4° C. The pelleted plasma membranes were resuspended in 0.3% (w/v) CHAPS in phosphate buffered saline (PBS), sonicated, and then centrifuged at 13,000×g for 30 min to remove insoluble material. Aliquots of the extract were prepared for electrophoresis in SDS sample buffer. Some samples were further prepared by boiling, or by boiling and reduction with fresh $\beta$-mercaptoethanol. A 4% SDS-polyacrylamide stacking gel, and a continuous 10% separating gel were used in all cases. Proteins separated by PAGE were electrophoretically transferred to a PVDF membrane (BioRad) using standard techniques. The membranes were cut into strips, blocked overnight with 5% nonfat dry milk-PBS-Tween, and then incubated with hybridoma culture supernatant diluted 1:100 in 5% (w/v) nonfat dry milk in PBS-Tween for 1 hour on a shaker plate at 25° C. Control experiments used irrelevant primary antibody SB-1, which specifically binds chicken alkaline phosphatase (Bruder and Caplan, 1990), or no McAb at all. Following thorough washing of PVDF membranes with PBS, detection of bound primary antibody was performed according to the VectaStain Elite ABC Kit instructions (Vector Labs).

Figure 1:
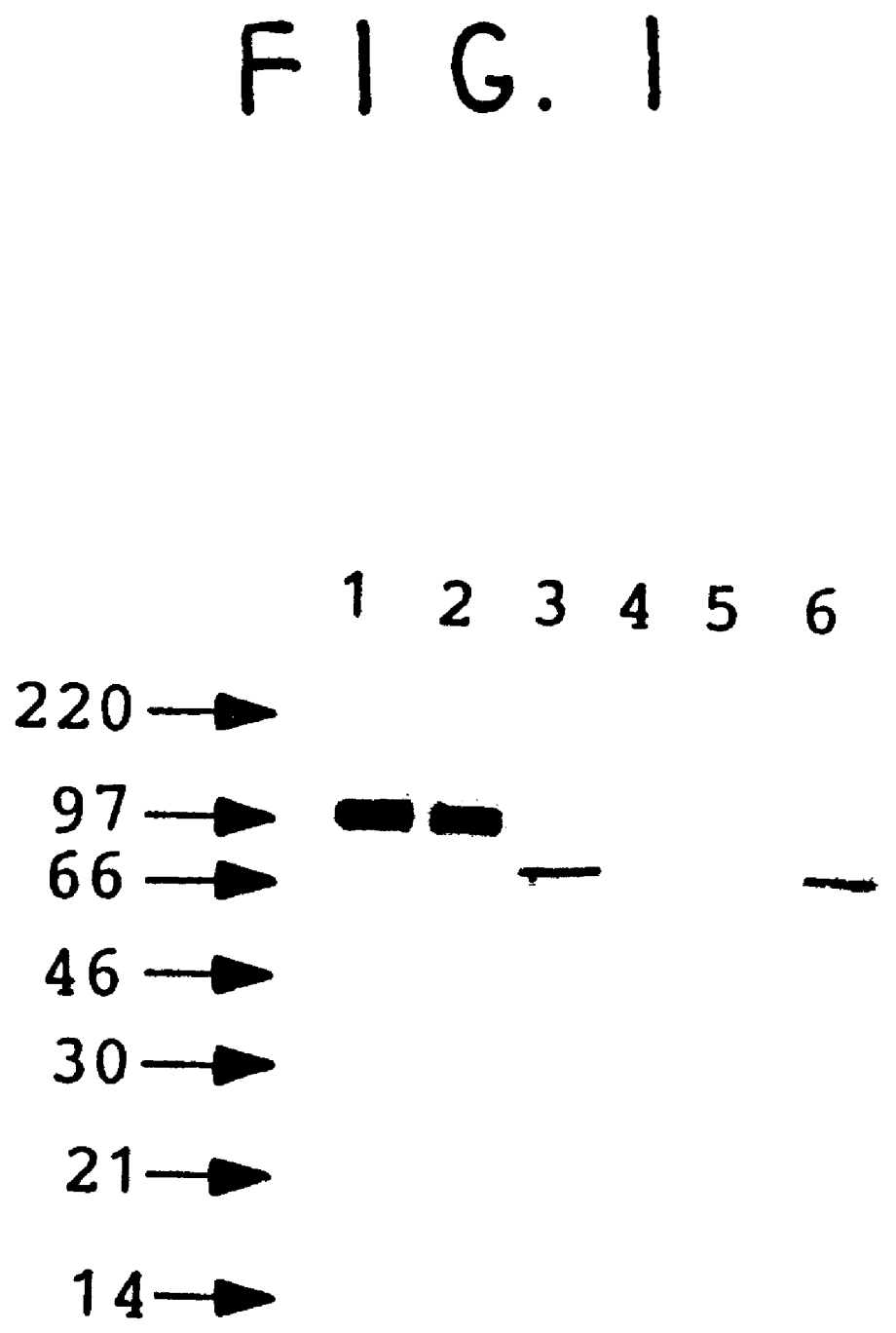

Immunoblots of human MSC plasma membranes, extracted with 0.3% CHAPS, and probed with antibody SB-10, showed a specific immunoreactive band at an apparent molecular weight of ~99 kDa (FIG. 1). The position and intensity of this band did not change when the extract was denatured by boiling; however, immunoreactivity was completely abolished when the extract was reduced with $\beta$-mercaptoethanol prior to electrophoresis. To compare the antigen present on cultured MSCs with the antigen recognized in cryosections of limb and lung, extracts of these human fetal tissues were prepared, and similarly probed with SB-10. A specific immunoreactive band migrating at an apparent molecular weight of ~99 kDa was also present in both the lung and limb extracts (data not shown).

EXAMPLE 2

Immunoprecipitation, Antigen Purification and Peptide Sequence Analysis

CHAPS-soluble MSC membrane extract (~27 mg) from ~1.5×10$^8$ cells was incubated with 200 $\mu$g of purified SB-10 antibody for 1 hr at 4° C. A 200 $\mu$l slurry of Protein-G Sepharose (Boehringer Mannheim) was added, and the mixture was incubated in rotation for 16 hr at 4° C. The resin was washed exhaustively with fresh lysis buffer containing 0.3% CHAPS, and the affinity-bound material was eluted by boiling for 5 min in SDS sample buffer. Following unreduced SDS-PAGE of the eluted material, gels were stained briefly with 0.05% Coomassie-G in 5% acetic acid/10% methanol, destained in 5% acetic acid/10% methanol, and the ~99 kDa bands from five identical preparations were excised. In-gel digestion was carried out using lysine C-endoproteinase (WAKO) (Rosenfeld et al., 1992). HPLC separations were performed on a Hewlett-Packard 1090 LC system using a Vydac C18 column (2.1 mm ×250 mm). The separated peptides were then subjected to N-terminal amino acid sequence analysis using a Hewlett-Packard G1005A Sequencing System.

Antibody SB-10 and irrelevant control immunoprecipitates were prepared from MSCs as described above. The cell extracts were pre-treated with Protein-G Sepharose (Boehringer Mannheim) to remove any components which bound non-specifically. The affinity bound material was eluted by boiling in 25 µl 0.5% SDS solution for 5 min. The solution was briefly centrifuged and the supernatant was transferred to a new tube for alkylation and deglycosylation of the immunoprecipitates. Bovine fetuin was digested in parallel in order to confirm appropriate activity of the glycosidases. A 2.5 µl volume of 1M Tris pH 8.5 was added to each sample followed by 1 µl of 1% (v/v) triethylphosphine (Aldrich) in methanol and 1 µl of 1% (v/v) 4-vinylpyridine (Aldrich) in methanol. The reactions proceeded for 4 hours at 37° C. The volume of the samples was reduced by half in vacuo, after which, water was added to return to the original volume. A 10 µl volume of 7.5% (v/v) NP-40 was added to the solutions followed by a 15 hour digestion with 0.1 U N-glycosidase F (Boehringer Mannheim) at 37° C. The pH of the samples was adjusted to 7 by the addition of 1% (v/v) acetic acid (HPLC grade, VWR), and 2 hour digestion with 3.1 mU neuraminidase (Genzyme) was then performed. A final 15 hour digestion with 0.075 mU of O-glycanase (Genzyme) was performed at 37° C. Aliquots were removed after digestion with N-glycanase and O-glycanase for MALDI-TOF mass spectrometry.

Following precipitation of the immune complexes in MSC extracts incubated with antibody SB-10, the eluted proteins were separated by SDS-PAGE, stained with Coomassie-G, and the ~99 kDa fragment was excised from each gel (FIG. 2A). This process was repeated five times, and the samples pooled, in order to recover enough material for internal protein sequence analysis. Peptides generated by in-gel digestion with Lysine C endoproteinase were separated by reverse-phase HPLC (FIG. 2B). Eluted peaks were hand collected as individual fractions and subjected to N-terminal sequence analysis. The sequenced peptides were referred to as K1 through K8 (Table I).

A search of the Entrez database at the National Center for Biotechnology Information using the BLAST (Altschul et al., 1990) program revealed sequence identity with human ALCAM, whose GenBank accession number is L38608 (Bowen et al., 1995).

EXAMPLE 3

Mass Spectrometry

Matrix assisted laser desorption/ionization—time of flight (MALDI-TOF) mass spectrometry was performed using a Hewlett Packard G2025A instrument with version A.03.00 software. Immunoprecipitate samples were prepared for mass spectrometry using thin polycrystalline matrix films (Xiang and Beavis, 1994). A 0.8 µl volume of sinapinic acid solution (Hewlett Packard) was dried onto the G2025A mesa using a Hewlett Packard G2024A sample preparation station, and then gently crushed against a sheet of polypropylene plastic. A saturated solution of sinapinic acid (Aldrich) was also prepared in 3:2:1 isopropanol:water:formic acid (isopropanol, HPLC grade from VWR, Inc., formic acid from Aldrich), and the insoluble material was removed by two rounds of centrifugation at 13,000×g. A 1 µl volume of the antigen sample was then diluted with 1 µl of this sinapinic acid solution. A 0.8 µl volume of the resulting solution was applied to the crushed matrix on the mesa and allowed to evaporate in air until it reduced to approximately one third of its original volume. The mesa was then immersed for 2–3 seconds in 30 ml of 0.05% (v/v) trifluoroacetic acid (Pierce). The mesa was dried using the G2024A sample preparation station and loaded into the instrument. Spectra were acquired using a laser power of 11.2–11.4 µJ, with the number of shots accumulated indicated in the legend of FIG. 3.

MALDI-TOF mass spectrometry was performed on immunoprecipitated material. FIG. 3A shows that purified ALCAM, which migrates in SDS-polyacrylamide gels at a position corresponding to ~99 kDa, has a measured mass by MALDI of 80,303±195 Da. Reduction, alkylation, and removal of N-linked oligosaccharides reduces the mass to 63,590±44 Da (FIG. 3B). No further reduction in mass was observed following treatment with neuraminidase and O-glycanase, which remove sialic acid residues and O-linked oligosaccharides, respectively (FIG. 3C).

MALDI-TOF mass spectrometry demonstrates that the intact ALCAM molecule has a mass of 80,303±193 Da,

TABLE I

Sequence analysis of peptides derived from Lysine-C endoproteinase digestion of the SB-10 antigen.

| HPLC Fraction | Retention Time (min) | Peptide Sequences[a] | |
|---|---|---|---|
| K1 | 25.41 | (50)SVQYDDVPE | (SEQ ID NO:1) |
| K2 | 33.98 | (377)KRESLTKIVEGXP | (SEQ ID NO:2) |
|  |  | (61)DRLNLXEQYTLSIXNXRIXD | (SEQ ID NO:3) |
| K3 | 37.05 | (116)ALFLETE | (SEQ ID NO:4) |
|  |  | (34)PDGSPVFIAFRSST | (SEQ ID NO:5) |
| K4 | 38.17 | (416)PAIQWTITGSGSVI | (SEQ ID NO:6) |
| K5 | 40.27 | (185)ADIQMPFTXSVTYYGPSXQ | (SEQ ID NO:7) |
|  |  | (164)EMDPVTQLYTMTSXXE | (SEQ ID NO:8) |
|  |  | (127)LGDXISEDXY | (SEQ ID NO:9) |
| K6 | 45.51 | (243)XLGNGNPPPEEFLFY | (SEQ ID NO:10) |
|  |  | (205)TIHSEQAVFDIXY | (SEQ ID NO:11) |
|  |  | (446)IIISPEEXVTLTXXA | (SEQ ID NO:12) |
| K8 | 49.81 | (149)VLHPLEGAV | (SEQ ID NO:13) |

[a]The numbers in parentheses refer to the residue number when aligned with the mature human ALCAM sequence. An "X" indicates the inability to assign an identity to a residue at that posifion.

although the apparent molecular weight under native or reducing conditions is ~99 kDa when analyzed by SDS-PAGE (Patel et al., 1995). Anomalous mobility of glycosylated proteins is common, e.g. COMP (Zaia et al., 1997), and the SB-10 antigen proved to have N-linked oligosaccharides. The reduction in mass following treatment of the sample with N-glycosidase accounts for a carbohydrate mass of 17,763±237 Da, after correcting for the mass of the alkylating groups. The mass observed after deglycosylation corresponds well to the predicted mass of the ALCAM core protein following modification of all ten cysteine residues with 4-vinylpyridine (66,343 Da). If all ten potential sites for N-linked carbohydrate moieties are occupied, the average mass of each of the carbohydrate chains would be 1,780 Da, a number within the commonly-observed size range for these substituents. Immunoblotting results also indicate that the antigenicity of the SB-10 epitope is dependent on disulfide linkages. Since ALCAM is known to have five immunoglobulin-like disulfide linkages in the extracellular domain, it likely that SB-10 recognizes one of these conformation-dependent regions.

EXAMPLE 4

Molecular Cloning of ALCAM cDNA from Human MSCs

A human MSC cDNA expression library was constructed using the λZAP vector system (Stratagene). PCR amplification of a 372 bp fragment specific for ALCAM was performed with the following 5' primer (5'-ATTATCATTTCCCCTGAAGAGAAT-3')(SEQ ID NO:14) and 3' primer (5'-GCCTAAGAGAGAAACTGTCCTAGTT-3')(SEQ ID NO:15). The resulting PCR product was cloned using the TA Cloning Kit (Invitrogen) and sequenced using Sequenase (U.S. Biochemical) to confirm the nucleotide sequence. The PCR product was labeled with $^{32}$P-dCTP and used to probe the human MSC cDNA library. Following secondary screening with the same probe, selected plaques were excised and reinfected into the SOLR strain of E. coli, restriction enzyme mapped, and selected clones were sequenced. Two clones with a common, unique internal restriction site were ligated together using T4 DNA Ligase (Gibco-BRL) to produce a full length cDNA for ALCAM. PCR oligonucleotides were designed with an Nco I site on the 5' primer (5'-CATGCCATGGCTCCGTCAGTGGCCCACC-3')(SEQ ID NO:16) and a BamHI site on the 3' primer (5'-CATGGATCCAACTAGGACAGTTTCTCTCTTAGG-3') (SEQ ID NO:17) to enable cloning into the pET-3d vector (Stratagene). PCR was performed with the addition of 5% glycerol and 0.1% BSA, with annealing at 60° C. Vent™ DNA Polymerase (New England Biolabs) was used to amplify the full length ALCAM clone to reduce the chance of mutations due to PCR error. The sequence was confirmed using the Prism™ 377 DNA Sequencer (Applied Biosystems).

Using cDNA from a human MSC expression library as a template, polymerase chain reaction (PCR) was performed with a 5' primer corresponding to peptide K6 which begins at residue 446 in human ALCAM (Table I), and with a 3' primer corresponding to the carboxy-terminal residue and a portion of the untranslated region of ALCAM. The resulting 372 bp PCR product was cloned, sequenced and found to match the published sequence of ALCAM exactly. Following screening of the cDNA library, reinfection into the SOLR strain of E. coli, and restriction enzyme mapping of selected clones, two clones with a common, unique internal restriction site were ligated together to produce a full length cDNA for human ALCAM. Complete sequence analysis of the full length clone confirmed identity with an ALCAM variant that contains a serine for asparagine substitution at residue 231 of the mature protein.

To verify that antibody SB-10 recognizes ALCAM, we performed a series of immunoblots with J4-81, an antibody known to react with ALCAM (Pesando et al., 1986). A standard CHAPS-soluble human MSC extract was subjected to immunoblotting, and a single band of reactivity at ~99 kDa was observed in samples incubated with either SB-10 or J4-81 (FIG. 4A). An additional set of experiments was carried out by first performing an immunoprecipitation with antibody SB-10, and then subjecting the eluted material to SDS-PAGE and immunoblotting with SB-10 and J4-81. FIG. 4B confirms that a single ~99 kDa band is specifically reactive with both SB-10 and J4-81. Additional bands present in the lanes exposed to these antibodies represent non-specific reactivity of secondary antibody which occurs in the presence of an irrelevant primary control antibody. Finally, immunostaining of fetal limb sections with J4-81 reveal a pattern which is identical to that observed with SB-10 (data not shown).

Molecular cloning of a full length cDNA from our human MSC expression library confirmed the nucleotide sequence identity with ALCAM. The isolated clone represents a valiant containing a substitution of serine for asparagine at residue 231; however, it is possible that additional forms may exist in the MSC cDNA library that correspond to the polymorphisms previously noted (Bowen et al., 1995). We determined that the mRNA coding for human ALCAM has an apparent size of 6.1 kb, whether derived from fetal tissue, cultured MSCs, or the HL60 cell line, a finding in contrast to that of Bowen and colleagues (1995), who estimated the size to be 5.2 kb. Using a PCR-based approach, we identified ALCAM homologues in rat, rabbit, and dog MSC cultures, each of which contain a single mRNA species of approximately 5.8 kb. One may therefore infer, from the highly conserved peptide sequence in different species, that ALCAM plays an important role in the development of a variety of mesenchymal tissues.

EXAMPLE 5

Identification of ALCAM Homologues in Human Fetal and Animal MSC Cultures

Total cellular RNA from dog, rabbit, and rat MSC cultures was prepared with Tri-Reagent™ (Molecular Research Center) and chloroform, and then precipitated with isopropanol. First strand cDNA synthesis was completed using SuperScript™ II Reverse Transcriptase (Gibco-BRL), and these cDNAs were employed as templates for PCR using oligonucleotide primers for the 372 bp fragment noted previously, and a 1593 bp fragment specific to ALCAM. The 5' primer for this 1593 bp fragment was (5'-GGCTCCCCAGTATTTATT-3')(SEQ ID NO:18), and the 3' primer was the same as that used for the 372 bp fragment. PCR products corresponding to ALCAM peptide fragments were generated, and then sequenced on an ABI Prism™ 377 DNA Sequencer to determine the extent of homology with human ALCAM.

Expression of ALCAM mRNA in selected human fetal tissues was confirmed by performing reverse transcriptase-PCR (RT-PCR) using oligonucleotide primers coding for the 372 bp fragment described above. FIG. 5A demonstrates amplification of this cDNA fragment from cultured human MSCs, and from samples of fetal limb periosteum, fetal lung and fetal CNS. These results correspond to the immunohistochemical staining that demonstrate ALCAM protein expression in these tissues (Bruder et al., 1997a).

MSC cultures from rabbit, rat, and dog marrow were also evaluated for the expression of ALCAM, or a homologous protein. Using oligonucleotide primers coding for ALCAM-specific fragments of 372 bp and 1593 bp, RT-PCR of mRNA from these cultures produced fragments of the appropriate size (FIG. 5B). Following PCR amplification of homologous ALCAM cDNAs in animal MSC cultures, sequence analysis was performed using a series of human ALCAM-based oligonucleotide primers. Primers corresponding to the amino terminal region of the human protein were not capable of supporting PCR amplification from animal mRNA. Hence, nucleotide sequence for the amino terminal residues corresponding to positions 1–63 of human ALCAM could not be determined in the animal samples. Nevertheless, we obtained reliable sequence data for rabbit and dog ALCAM homologues that map to the remaining 90% of the full length human cDNA. The nucleotide sequences translate to a protein sequence for rabbit ALCAM which is 95% identical and 97% similar to human ALCAM, and the dog sequence has 94% identity and 95% similarity to human ALCAM. ALCAM from rat MSCs showed similar homology, although a central region of the protein's nucleotide sequence could not be amplified by PCR using primers that were successful in human, rabbit, and dog samples. Of the 155 residues which were deduced for the rat, 89% were identical and 92% were similar to the corresponding region of human ALCAM. The final sequence determination for each species was verified by three independent nucleotide sequencing experiments. The nucleotide and protein sequence data reported in this paper appears in the EMBL, GenBank and DDBJ Nucleotide Sequence Databases under the accession numbers of Y13240 and Y13241 (rat), Y13242 (dog), and Y13243 (rabbit). Finally, Northern blot analysis of total RNA from human MSCs and fetal tissues demonstrates a single band migrating at an apparent size of ~6.1 kilobases (FIG. 5C). HL60 cells were also included as a positive control, since these cells have been shown to express ALCAM mRNA (Bowen et al., 1995). By contrast, the reactive mRNA observed in dog, rabbit, and rat MSCs is slightly smaller, migrating at ~5.8 kilobases.

Total cellular RNA from human MSCs, selected fetal tissues, and HL60 cells was prepared as described above for the dog, rabbit, and rat MSCs. Twenty μg of total RNA was fractionated on a 1% agarose gel containing 6.7% formaldehyde, and transferred to a Hybond-N$^+$ nylon membrane (Amersham). RNA was cross-linked to the membrane by baking at 80° C. in a vacuum oven, and probed with a random-primed, double-labeled ($^{32}$P-dCTP and $^{32}$P-dATP) ALCAM 372 bp PCR fragment. Membranes were exposed to phosphoimaging screens and then visualized on a STORM phosphoimaging unit (Molecular Dynamics).

EXAMPLE 6

SB 10 $F_{ab}$ Fragments Accelerate In Vitro Osteogenesis of Human MSCs

Human MSCs were directed into the osteogenic lineage in vitro by the addition of OS (100 nM dexamethasone, 10 mM βGP, and 50 μM ascorbic acid-2-phosphate), as previously described (Jaiswal et al., 1997). Cultures were assayed for alkaline phosphatase activity and mineral deposition according to established techniques (Jaiswal et al., 1997). Cultures grown under control or OS conditions were also incubated with $F_{ab}$ fragments of SB-10 and SB-1 at a concentration of 10 μg/ml. Fresh $F_{ab}$ fragments were added with each medium change, for a total of 12 days.

Since previous data indicates that ALCAM is capable of homophilic interactions (Bowen et al., 1995; Tanaka et al., 1991; Burns et al., 1991; Bajorath et al., 1995), and ALCAM expression is lost during the in vivo transition from osteoprogenitor to APase-positive pre-osteoblast (Bruder et al., 1997a), we evaluated the possibility that blocking homotypic ALCAM interactions would influence osteogenic differentiation. Using a model for in vitro differentiation of human MSCs (Jaiswal et al., 1997), we discovered that the addition of SB-10 $F_{ab}$ fragments significantly elevated the level and rate of APase protein expression during osteogenesis (Table II).

TABLE II

Alkaline phosphatase activity and calcium deposition in MSC cultures grown in the presence and absence of anti-ALCAM $F_{ab}$ fragments

| Treatment | APase activity (nmol/min) |
|---|---|
| Day 6 | |
| Control | 1.13 ± 0.10 |
| OS | 2.15 ± 0.16* |
| OS + SB-10 $F_{ab}$ | 2.72 ± 0.11*† |
| OS + SB-1 $F_{ab}$ | 2.24 ± 0.23* |
| Day 12 | |
| Control | 3.49 ± 0.13 |
| OS | 11.47 ± 0.93* |
| OS + SB-10 $F_{ab}$ | 19.20 ± 1.59*† |
| OS + SB-1 $F_{ab}$ | 6.34 ± 1.77† |

Cells were seeded at $3 \times 10^3/cm^2$ and treated continuously with 10 μg/ml of antibody SB-10 (anti-ALCAM) or SB-1 (anti-chicken alkaline phosphatase). Cultures were assayed for APase and calcium deposition as described herein. The results represent the mean±SD of triplicate cultures of one representative donor. *p<0.05, compared to Control.; †p<0.05, compared to OS treated cultures. At day 6, OS and OS+SB-1 were not statistically different.

After 6 days in culture, the addition of SB-10 $F_{ab}$ fragments to medium containing osteogenic supplements [OS] increased APase activity significantly when compared to those cultures exposed to OS alone. By day 12, APase activity in samples receiving the SB-10 $F_{ab}$s was almost twice that present in cultures containing only OS. The percentage of cells in the dish which were stained for APase also increased in the presence of SB-10 $F_{ab}$ s but not when SB-1 (control) $F_{ab}$s were added. Furthermore, SB-10 $F_{ab}$ fragments accelerated the terminal differentiation events, as noted by the early deposition of mineralized extracellular matrix. Cultures grown under control, OS, or OS plus SB-10 $F_{ab}$ treated conditions did not contain detectable calcium by day 12; however, samples incubated in the presence of SB-10 $F_{ab}$s plus OS contained a substantial amount of mineral (6.76±1.28 μg of calcium/dish). The addition of SB-10 or SB-1 $F_{ab}$s to control cultures had no effect on APase activity or mineral deposition (data not shown).

In summary, our results confirm that the addition of SB-10 (anti-ALCAM) $F_{ab}$ fragments to human MSCs undergoing osteogenesis in vitro stimulates the differentiation process. Expression of cell surface APase is more abundant, and occurs sooner in cultures exposed to SB-10 $F_{ab}$s than cultures treated with control $F_{ab}$s.

CITED LITERATURE

Altschul, S. F., Gish, W., Miller, W., Myers, E. W., and Lipman, D. J. (1990). Basic local alignment search tool. J. Mol. Biol. 215:403–10.

Bajorath, J., Bowen, M. A., and Aruffo, A. (1995) Molecular model of the N-terminal receptor-binding domain of the human CD6 ligand ALCAM. Protein Sci., 4(8), 1644–1647.

Benayahu, D., Efrati, M., and Weintroub, S. (1995) Monoclonal antibodies recognize antigen expressed by osteoblasts. J. Bone Miner. Res., 10, 1496–1503.

Bowen, M. A. Patel, D. D., Li, X., Modrell, B., Malacko, A. R., Wang, W. C., Marquardt, H., Neubauer, M., Pesando, J. M., Francke, U., Haynes, B. F., and Aruffo, A. (1995) Cloning, mapping, and characterization of activated leukocyte-cell adhesion molecule (ALCAM), a CD6 ligand. J. Exp. Med., 181, 2213–2220.

Bruder, S. P., and Caplan, A. I. (1990) A monoclonal antibody against the surface of osteoblasts recognizes alkaline phosphatase isoenzymes in bone, liver, kidney and intestine. Bone., 11,133–139.

Bruder, S. P., Horowitz, M. C., Mosca, J. D., and Haynesworth, S. E. (1997a) Monoclonal antibodies reactive with human osteogenic cell surface antigens. Bone, 19, (in press).

Bruder, S. P., Jaiswal, N., and Haynesworth, S. E. (1997b) Growth kinetics, self-renewal and the osteogenic potential of purified human mesenchymal stem cells during extensive subcultivation and following cryopreservation. Journal of Cellular Biochemistry: 64(2), 278–294.

Burns, F. R., von Kannen, S., Guy, L., Raper, J. A., Kamholz, J., and Chang, S. (1991) DM-GRASP, a novel immunoglobulin superfamily axonal surface protein that supports neurite extension. Neuron, 7(2), 209–220.

Caplan, A. I. (1991) Mesenchymal stem cells. J. Orthop. Res., 9,641–650.

Caplan, A. I., Fink, D. J., Goto, T., Linton, A. E., Young, R. G., Wakitani, S., Goldberg, V. M., and Haynesworth, S. E. (1993) Mesenchymal stem cells and tissue repair. In Jackson, D. W. (ed.) *The Anterior Cruciate Ligament: Current and Future Concepts.* Raven Press, Ltd., New York. pp. 405–417.

Dennis, J. E., Haynesworth, S. E., Young, R. G., and Caplan, A. I. (1992) Osteogenesis in marrow-derived mesenchymal cell porous ceramic composites transplanted subcutaneously: Effect of fibronectin and laminin on cell retention and rate of osteogenic expression. Cell Transplant, 1, 23–32.

Gronthos, S., Graves, S. E., Ohta, S., and Simmons, P. J. (1994) The STRO-1+ fraction of adult human bone marrow contains the osteogenic precursors. Blood, 84, 4164–4173.

Haynesworth, S. E., Baber, M. A., and Caplan, A. I. (1992a) Cell surface antigens on human marrow-derived mesenchymal cells are detected by monoclonal antibodies. Bone, 13, 69–80.

Haynesworth, S. E., Goshima, J., Goldberg, V. M., and Caplan, A. I. (1992b) Characterization of cells with osteogenic potential from human marrow. Bone., 13, 81–88.

Jaiswal, N., Haynesworth, S. E., Caplan, A. I., and Bruder, S. P. (1997) Osteogenic differentiation of purified, culture-expanded human mesenchymal stem cells in vitro. Journal of Cellular Biochemistry, 64(2), 295–312.

Johnstone, B., Yoo, J. U., and Barry, F. P. (1996) In vitro chondrogenesis of bone marrow-derived mesenchymal cells. Trans. Ortho. Res. Soc., 21, 65.

Kadiyala, S., Young, R. G., Thiede, M. A., and Bruder, S. P. (1997) Culture-Expanded Canine Mesenchymal Stem Cells Possess Osteochondrogenic Potential In Vivo and In Vitro. Cell Transplantation., 6, 125–134.

Laesing, U., Giordano, S., Stecher, B., Lottspeich, F., and Stuermer, C. A. O. (1994) Molecular characterization of fish neurolin: A growth-associated cell surface protein and member of the immunoglobulin superfamily in the fish retinotectal system with similarities to chick protein DM-GRASP/SC-1/BEN. Differentiation, 56, 21–29.

Lee, Y. S., and Chuong, C. M. (1992) Adhesion molecules in skeletogenesis: I. Transient expression of neural cell adhesion molecule (NCAM) in osteoblasts during endochondral and intramembranous ossification. J. Bone Miner. Res., 7(12), 1435–1446.

Lehmann, J. M., Riethmuller, G., and Johnson, J. (1989) MUC18, a marker of tumor progression in human melanoma, shows sequence similarity to the neural cell adhesion molecules of the immunoglobulin superfamily. Proc. Natl. Acad. Sci. USA, 86, 9891–9895.

Lennon, D. P., Haynesworth, S. E., Bruder, S. P., Jaiswal, N., and Caplan, A. I. (1996) Development of a serum screen for mesenchymal progenitor cells from bone marrow. In Vitro Animal Cellular & Developmental Biology, 32(10), 602–611.

Majumdar, M. K., Haynesworth, S. E., Thiede, M. A., Marshak, D. R., Caplan, A. I., and Gerson, S. L. (1995) Culture-expanded human mesenchymal stem cells (MSCs) express cytokines and support hematopoiesis in vitro. Blood, 86(10), 494a, #1966.

Nakahara, H., Bruder, S. P., Goldberg, V. M., and Caplan, A. I. (1990) In vivo osteochondrogenic potential of cultured cells derived from the periosteum. Clin. Orthop. Rel. Res., 259, 223–232.

Okazaki, M., Takeshita, S., Kawai, S., Kikuno, R., Tsujimura, A., Kudo, A., and Amann, E. (1994) Molecular cloning and characterization of OB-Cadherin, a new member of cadherin family expressed in osteoblasts. J. Biol. Chem., 269(16), 12092–12098.

Owen, M. (1985) Lineage of osteogenic cells and their relationship to the stromal system. In Peck, W. A. (ed.) *Bone and Mineral/3* Elsevier, Amsterdam, pp. 1–25.

Patel, D. D., Wee, S. F., Whichard, L. P., Bowen, M. A., Pesando, J. M., Aruffo, A., and Haynes, B. F. (1995) Identification and characterization of a 100 kDa ligand for CD6 on human thymic epithelial cells. J. Exp. Med., 181, 1563–1568.

Pereira, R. F., Halford, K. W., O'Hara, M. D., Leeper, D. B., Sokolov, B. P., Pollard, M. D., Bagasra, O., and Prockop, D. J. (1995) Culture adherent cells from marrow can serve as long-lasting precursor cells for bone, cartilage, and lung in irradiated mice. Proc. Natl. Acad. Sci. USA., 92, 4857–4861.

Pesando, J. M., Hoffman, P., and Abed, M. (1986) Antibody-induced antigenic modulation is antigen dependent: characterization of 22 proteins on a malignant human B cell line. J. Immunol., 137, 3689–3695.

Pittenger, M. F., Mackay, A. M., and Beck, S. C. (1996) Human mesenchymal stem cells can be directed into chondrocytes, adipocytes and osteocytes. *Mol. Biol. Cell.,* 7, 305a.

Pourquie, O., Corbel, C., Le Care, J. P., Rossier, F., and Le Dourain, N. M. (1992) BEN, a surface glycoprotein of the immunoglobulin superfamily, is expressed in a variety of developing systems. Proc, Natl, Acad, Sci, USA, 89, 5261–5265.

Resnick, D., Pearson, A., and Krieger, M. (1994) The SRCR superfamily: a family reminiscent of the Ig superfamily. Trends Biochem. Sci., 19, 5–8.

Rosenfeld, J., Capdevielle, J., Guillemot, J. C., and Ferrara, P. (1992) In-gel digestion of proteins for internal sequence analysis after one- or two-dimensional gel electrophoresis. Anal. Biochem., 203, 173–179.

Simmons, P. J., and Torok-Storb, B. (1991) Identification of stromal cell precursors in human bone marrow by a novel monoclonal antibody, STRO-1. Blood, 78, 55–62.

Tanaka, H., Matsui, T., Agata, A., Tomura, M., Kubota, I., McFarland, K. C., Kohr, B., Lee, A., Phillips, H. S., and Shelton, D. L. (199 1) Molecular cloning and expression of a novel adhesion molecule, SCl. Neuron, 7(4), 535–545.

Tanaka, Y., Morimoto, I., Nakano, Y., Okada, Y., Hirota, S., Nomura, S., Nakamura, T., and Eto, S. (1995) Osteoblasts are regulated by the cellular adhesion through ICAM-1 and VCAM-1. J. Bone Miner. Res., 10(10), 1462–1469.

Wakitani, S., Goto, T., Pineda, S. J., Young, R. G., Mansour, J. M., Goldberg, V. M., and Caplan, A. I. (1994) Mesenchymal cell-based repair of large full-thickness defects of articular cartilage. J. Bone Joint Surg., 76, 579–592.

Wakitani, S., Saito, T., and Caplan, A. I. (1995) Myogenic cells derived from rat bone marrow mesenchymal stem cells exposed to 5-azacytidine. Muscle & Nerve, 18, 1417–1426.

Xiang, F., and Beavis, R. C. (1994) A method to increase contaminant tolerance in protein matrix-assisted laser desorption/ionization by the fabrication of thin protein-doped polycrystalline films. Rapid Commun. Mass Spectrom., 8, 199–204.

Young, R. G., Butler, D. L., Weber, W., Gordon, S. L., and Fink, D. J. (1997) Mesenchymal stem cell-based repair of rabbit achilles tendon. Trans. Ortho. Res. Soc., 22, 249.

Zaia, J., Boynton, R. E., McIntosh, A., Marshak, D. R., Olsson, H., Heinegård, D. and Barry, F. (1997) Post-translational modifications in cartilage oligomeric matrix protein. J. Biol. Chem., in press.

What is claimed is:

1. A composition comprising an ALCAM-bearing mesenchymal stem cell and a ligand that binds with ALCAM on a single mesenchymal stem cell.

2. The composition of claim 1 wherein the mesenchymal stem cell is human.

3. The composition of claim 1 wherein the ligand is an $F_{ab}$ fragment of an antibody to ALCAM.

4. The composition of claim 3 wherein antibody is produced by the cell line deposited under ATCC Accession No. HB 11789.

5. The composition of claim 1 wherein the ligand is a single chain antibody to ALCAM.

6. A composition comprising an ALCAM-bearing mesenchymal stem cell, an agent that is osteoinductive for said mesenchymal stem cell and a ligand that binds with ALCAM on a single mesenchymal stem cell.

7. The composition of claim 6 wherein the ligand is an $F_{ab}$ fragment of an antibody to ALCAM.

8. The composition of claim 7 wherein the antibody is produced by the cell line deposited under ATCC Accession No. HB 11789.

9. The composition of claim 6 wherein the ligand is a single chain antibody to ALCAM.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 9 AMINO ACIDS
      (B) TYPE: AMINO ACID
      (C) STRANDEDNESS: <Unknown>
      (D) TOPOLOGY: LINEAR (ii) MOLECULE TYPE: polypeptide (xi) SEQUENCE DESCRIPTION: SEQ ID NO: 1:

Ser Val Gln Tyr Asp Asp Val Pro Glu
                5

(2) INFORMATION FOR SEQ ID NO: 2:

(i) SEQUENCE CHARACTERISTICS:
      (A) LENGTH: 13 AMINO ACIDS
      (B) TYPE: AMINO ACID
      (C) STRANDEDNESS: <Unknown>
      (D) TOPOLOGY: LINEAR (ii) MOLECULE TYPE: polypeptide (xi) SEQUENCE DESCRIPTION: SEQ ID NO: 2:

Lys Arg Glu Ser Leu Thr Lys Ile Val Glu Gly Xaa Pro
            5                  10

(2) INFORMATION FOR SEQ ID NO: 3:

(i) SEQUENCE CHARACTERISTICS:
      (A) LENGTH: 20 AMINO ACIDS
      (B) TYPE: AMINO ACID
      (C) STRANDEDNESS: <Unknown>
      (D) TOPOLOGY: LINEAR (ii) MOLECULE TYPE: polypeptide (xi) SEQUENCE DESCRIPTION: SEQ ID NO: 3:

Asp Arg Leu Asn Leu Xaa Glu Gln Tyr Thr Leu Ser Ile Xaa Asn Xaa
            5                10            15

Arg Ile Xaa Asp
      20

(2) INFORMATION FOR SEQ ID NO: 4:

(i) SEQUENCE CHARACTERISTICS:
        (A) LENGTH: 7 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 4:

Ala Leu Phe Leu Glu Thr Glu
                 5

(2) INFORMATION FOR SEQ ID NO: 5:

(i) SEQUENCE CHARACTERISTICS:
        (A) LENGTH: 14 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 5:

Pro Asp Gly Ser Pro Val Phe Ile Ala Phe Arg Ser Ser Thr
               5                 10

(2) INFORMATION FOR SEQ ID NO: 6:

(i) SEQUENCE CHARACTERISTICS:
        (A) LENGTH: 14 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 6:

Pro Ala Ile Gln Trp Thr Ile Thr Gly Ser Gly Ser Val Ile
               5                 10

(2) INFORMATION FOR SEQ ID NO: 7:

(i) SEQUENCE CHARACTERISTICS:
        (A) LENGTH: 19 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 7:

Ala Asp Ile Gln Met Pro Phe Thr Xaa Ser Val Thr Tyr Tyr Gly Pro
               5                10              15

Ser Xaa Gln (2) INFORMATION FOR SEQ ID NO: 8:

(i) SEQUENCE CHARACTERISTICS:
        (A) LENGTH: 16 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 8:

Glu Met Asp Pro Val Thr Gln Leu Tyr Thr Met Thr Ser Xaa Xaa Glu
                  5                   10                  15

(2) INFORMATION FOR SEQ ID NO: 9:

(i) SEQUENCE CHARACTERISTICS:
        (A) LENGTH: 10 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 9:

Leu Gly Asp Xaa Ile Ser Glu Asp Xaa Tyr
                  5                   10

(2) INFORMATION FOR SEQ ID NO: 10:

(i) SEQUENCE CHARACTERISTICS:
        (A) LENGTH: 15 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 10:

Xaa Leu Gly Asn Gly Asn Pro Pro Glu Glu Phe Leu Phe Tyr
                  5                   10                  15

(2) INFORMATION FOR SEQ ID NO: 11:

(i) SEQUENCE CHARACTERISTICS:
        (A) LENGTH: 13 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 11:

Thr Ile His Ser Glu Gln Ala Val Phe Asp Ile Xaa Tyr
                  5                   10

(2) INFORMATION FOR SEQ ID NO: 12:

(i) SEQUENCE CHARACTERISTICS:
        (A) LENGTH: 15 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 12:

Ile Ile Ile Ser Pro Glu Glu Xaa Val Thr Leu Thr Xaa Xaa Ala
                  5                   10                  15

(2) INFORMATION FOR SEQ ID NO: 13:

(i) SEQUENCE CHARACTERISTICS:
        (A) LENGTH: 9 AMINO ACIDS
        (B) TYPE: AMINO ACID
        (C) STRANDEDNESS: <Unknown>
        (D) TOPOLOGY: LINEAR (ii) MOLECULE TYPE: peptide (xi) SEQUENCE DESCRIPTION: SEQ ID NO: 13:

Val Leu His Pro Leu Glu Gly Ala Val
                5

(2) INFORMATION FOR SEQ ID NO: 14:

(i) SEQUENCE CHARACTERISTICS:
        (A) LENGTH: 24 NUCLEOTIDES
        (B) TYPE: NUCLEIC ACID
        (C) STRANDEDNESS: SINGLE
        (D) TOPOLOGY: LINEAR (ii) MOLECULE TYPE: oligonucleotide (xi) SEQUENCE DESCRIPTION: SEQ ID NO: 14:

ATTATCATTT CCCCTGAAGA GAAT                                       24

(2) INFORMATION FOR SEQ ID NO: 15:

(i) SEQUENCE CHARACTERISTICS:
        (A) LENGTH: 25 NUCLEIC ACIDS
        (B) TYPE: NUCLEIC ACID
        (C) STRANDEDNESS: single
        (D) TOPOLOGY: LINEAR (ii) MOLECULE TYPE: oligonucleotide (xi) SEQUENCE DESCRIPTION: SEQ ID NO: 15:

GCCTAAGAGA GAAACTGTCC TAGTT                                      25

(2) INFORMATION FOR SEQ ID NO: 16:

(i) SEQUENCE CHARACTERISTICS:
        (A) LENGTH: 28 NUCLEIC ACIDS
        (B) TYPE: NUCLEIC ACID
        (C) STRANDEDNESS: SINGLE
        (D) TOPOLOGY: LINEAR (ii) MOLECULE TYPE: OLIGONUCLEOTIDE (xi) SEQUENCE DESCRIPTION: SEQ ID NO: 16:

CATGCCATGG CTCCGTCAGT GGCCCACC                                   28

(2) INFORMATION FOR SEQ ID NO: 17:

(i) SEQUENCE CHARACTERISTICS:
        (A) LENGTH: 33 NUCLEIC ACIDS
        (B) TYPE: NUCLEIC ACID
        (C) STRANDEDNESS: SINGLE
        (D) TOPOLOGY: LINEAR (ii) MOLECULE TYPE: oligonucleotide (xi) SEQUENCE DESCRIPTION: SEQ ID NO: 17:

CATGGATCCA ACTAGGACAG TTTCTCTCTT AGG                             33

(2) INFORMATION FOR SEQ ID NO: 18:

(i) SEQUENCE CHARACTERISTICS:
        (A) LENGTH: 18 NUCLEIC ACIDS
        (B) TYPE: NUCLEIC ACID
        (C) STRANDEDNESS: SINGLE
        (D) TOPOLOGY: LINEAR

-continued (ii) MOLECULE TYPE: OLIGONUCLEOTIDE (xi) SEQUENCE DESCRIPTION: SEQ ID NO: 18:

GGCTCCCCAG TATTTATT                                                                 18